(12) United States Patent
Goodin

(10) Patent No.: US 7,597,709 B2
(45) Date of Patent: *Oct. 6, 2009

(54) INNER MEMBER SUPPORT BLOCK

(75) Inventor: Richard L. Goodin, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 902 days.

This patent is subject to a terminal disclaimer.

(21) Appl. No.: 11/093,887

(22) Filed: Mar. 30, 2005

(65) Prior Publication Data

US 2005/0171571 A1    Aug. 4, 2005

Related U.S. Application Data

(63) Continuation of application No. 10/041,847, filed on Oct. 24, 2001, now Pat. No. 6,962,597.

(51) Int. Cl.
*A61F 6/06* (2006.01)
*A61M 29/00* (2006.01)

(52) U.S. Cl. .................. 623/1.11; 606/192

(58) Field of Classification Search ........... 623/1.11; 606/108, 192, 194
See application file for complete search history.

(56) References Cited

U.S. PATENT DOCUMENTS

| | | | |
|---|---|---|---|
| 4,413,989 A | 11/1983 | Schjeldahl et al. | |
| 4,813,930 A | 3/1989 | Elliott | |
| 4,917,666 A | 4/1990 | Solar et al. | |
| 4,950,227 A | 8/1990 | Savin et al. | |
| 4,955,895 A | 9/1990 | Sugiyama et al. | |
| 5,032,113 A | 7/1991 | Burns | |
| 5,098,412 A | 3/1992 | Shiu | |
| 5,176,637 A * | 1/1993 | Sagae | 604/103.14 |
| 5,324,263 A | 6/1994 | Kraus et al. | |
| 5,382,234 A | 1/1995 | Cornelius et al. | |
| 5,476,477 A | 12/1995 | Burns | |
| 5,911,715 A | 6/1999 | Berg et al. | |
| 5,968,069 A * | 10/1999 | Dusbabek et al. | 606/194 |
| 5,989,218 A | 11/1999 | Wasicek | |
| 6,066,114 A | 5/2000 | Goodin et al. | |
| 6,066,157 A | 5/2000 | Barbere | |
| 6,090,126 A | 7/2000 | Burns | |
| 6,419,685 B2 | 7/2002 | Di Caprio et al. | |
| 6,514,228 B1 | 2/2003 | Hamilton et al. | |
| 6,663,660 B2 | 12/2003 | Dusbabek et al. | |
| 6,702,802 B1 | 3/2004 | Hancock et al. | |
| 2002/0095203 A1 * | 7/2002 | Thompson et al. | 623/1.11 |

FOREIGN PATENT DOCUMENTS

| | | |
|---|---|---|
| EP | 0 405 831 A2 | 1/1991 |
| WO | WO 00/51674 | 9/2000 |

* cited by examiner

*Primary Examiner*—Todd E Manahan
*Assistant Examiner*—Jonathan A Hollm
(74) *Attorney, Agent, or Firm*—Crompton, Seager & Tufte, LLC

(57) ABSTRACT

An angioplasty catheter and method for making and using the same. An angioplasty catheter comprises an inner tube having a proximal end, a distal end, and a lumen extending therethrough; an outer tube disposed over the inner tube, the outer tube having a proximal end and a distal end; a balloon coupled to the distal end of the outer tube; an inflation lumen defined between the inner tube and the outer tube, the inflation balloon in fluid communication with the balloon; and a support block coupled to the inner tube. In addition, a method for manufacturing an angioplasty catheter is disclosed.

18 Claims, 2 Drawing Sheets

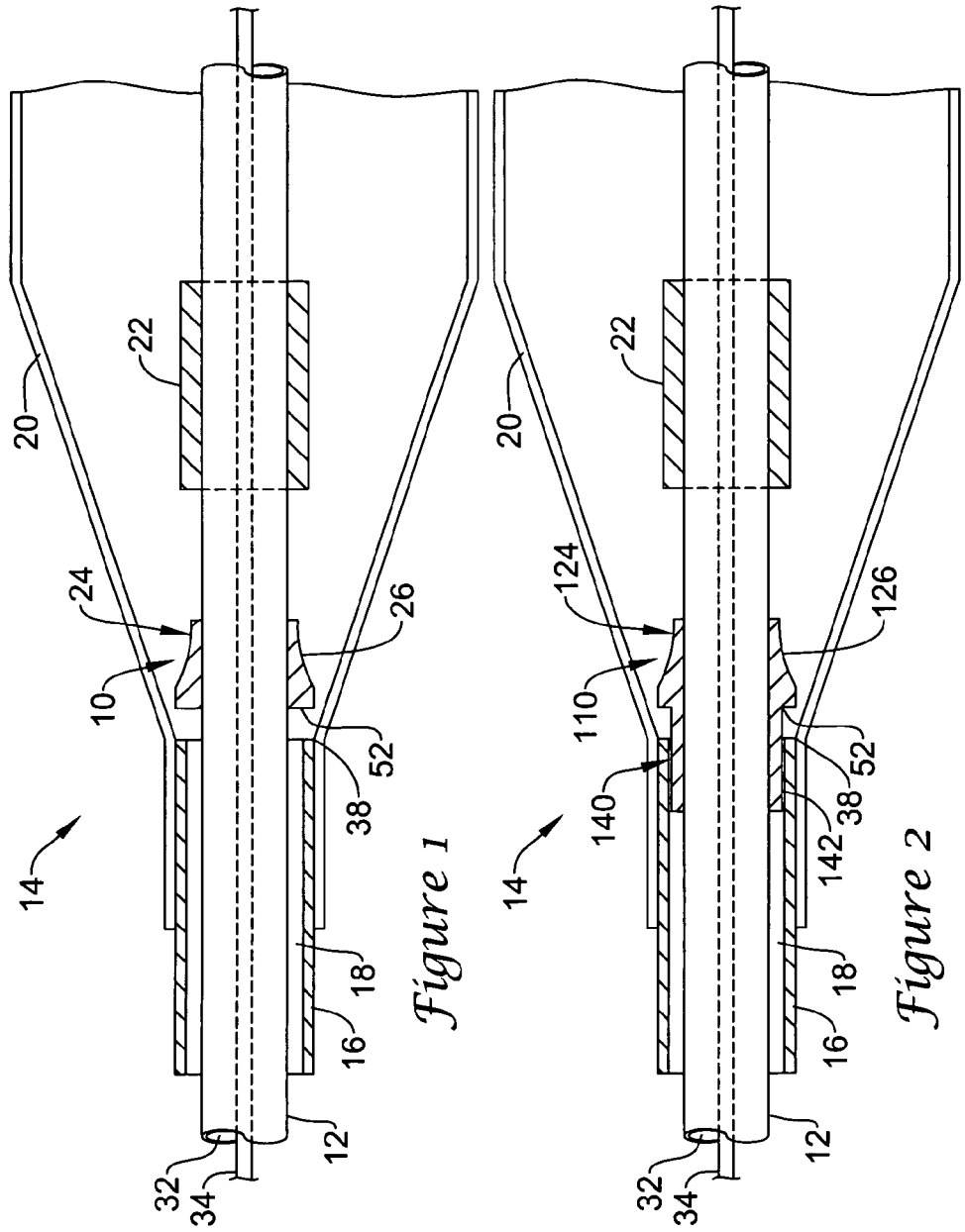

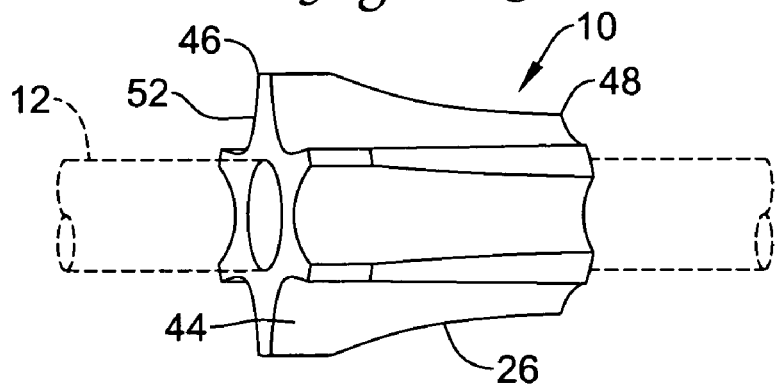
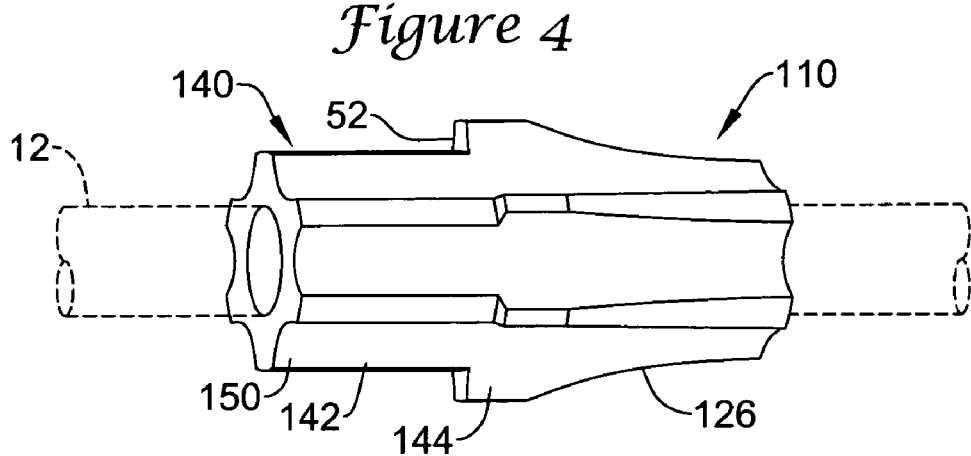
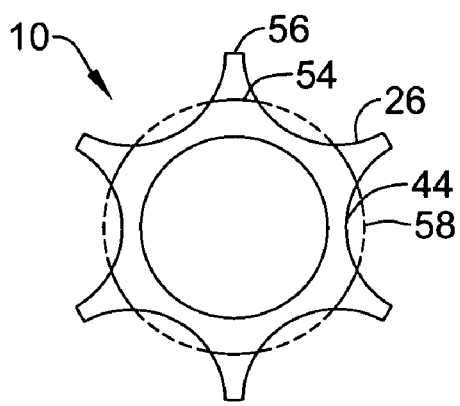
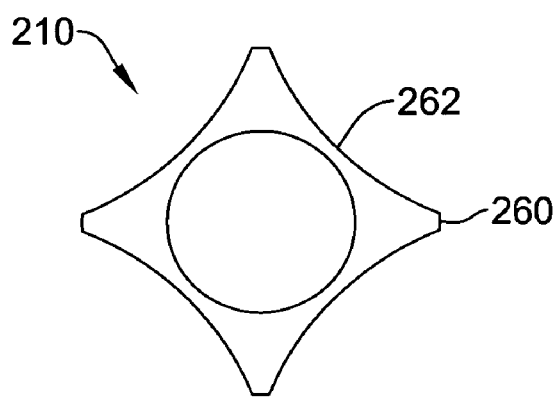

INNER MEMBER SUPPORT BLOCK

CROSS-REFERENCE TO CO-PENDING APPLICATION

This application is a continuation of U.S. application Ser. No. 10/041,847, filed Oct. 24, 2001 now U.S. Pat. No. 6,962,597, the entire disclosure of which is incorporated herein by reference.

FIELD OF THE INVENTION

The present invention pertains to angioplasty catheters. More particularly, the present invention pertains to angioplasty catheters with improved resistance to balloon and catheter deformation.

BACKGROUND OF THE INVENTION

The use of intravascular catheters has become an effective method for treating many types of vascular disease. In general, an intravascular catheter is inserted into the vascular system of a patient and navigated through the vasculature to a desired target site. Using this method, virtually any target site in a patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

The catheter may enter the patient's vasculature at a convenient location, and then be urged to a target region over a guidewire. Frequently, the path taken by a catheter through the vascular system is tortuous, requiring the guidewire to change direction frequently. Moreover, the catheter may confront a stenosis or a total occlusion when passing through the vasculature.

The success of the intravascular procedure often depends on the ability of the catheter to pass the stenosis. A clinician may need to apply significant force to the catheter in order to urge it through the stenosis. If the catheter is an angioplasty catheter, the act of attempting to pass the catheter through the stenosis may cause significant damage to the catheter, and may even make it inoperable. A need, therefore, exists for an angioplasty catheter with increased structural support.

SUMMARY OF THE INVENTION

The present invention pertains to angioplasty catheters. More particularly, the present invention comprises a refinement of angioplasty catheters that may include enhanced structural support. The present invention includes an angioplasty catheter with improved resistance to balloon deformation, improved prevention of occlusion of lumens (e.g., inflation lumens), and other refinements to the manufacturing of angioplasty catheters.

In a preferred embodiment, an angioplasty catheter may comprise an inner tube, an outer tube disposed over the inner tube, a balloon coupled to the outer tube, and an inflation lumen defined between the inner tube and the outer tube that is in fluid communication with the balloon. A support block may be coupled to the inner tube. The support block may substantially prevent occlusion of the inflation lumen during coupling of the balloon to the outer tube. In addition, the support block prevents a marker band from substantially occluding the inflation lumen.

The support block may include a distal region that may have a plurality of distal fins. Moreover, the support block may further comprise a proximal region that may have a plurality of proximal fins. The distal fins and/or the proximal fins may be collapsible.

The support block may be coupled to the inner tube by injection molding. Alternatively, the support block may be comprised of heat shrinkable material and wherein the support block is coupled to the inner tube by heat shrinking. In another alternative embodiment, the support block may be coupled to the inner tube by adhesive or by laser bonding.

BRIEF DESCRIPTION OF THE DRAWINGS

FIG. 1 is a plan view of an inner member support block according to a preferred embodiment of the invention;

FIG. 2 is a plan view of an alternative inner member support block according to a preferred embodiment of the invention;

FIG. 3 is a perspective view of the inner member support block shown in FIG. 1;

FIG. 4 is a perspective view of the inner member support block shown in FIG. 2;

FIG. 5 is a cross-sectional view of the inner member support block shown in FIG. 3; and FIG. 6 is a cross-sectional view of a second alternative inner member support block according to a preferred embodiment of the invention.

DETAILED DESCRIPTION OF THE PREFERRED EMBODIMENTS

The following description should be read with reference to the drawings wherein like reference numerals indicate like elements throughout the several views. The detailed description and drawings represent select embodiments and are not intended to be limiting.

FIG. 1 is a plan view of an inner member support block according to a preferred embodiment of the invention. A inner member support block 10 may be coupled to an inner tube 12 and may provide structural support during manufacturing or use of a catheter 14 (e.g., an intravascular catheter, an angioplasty catheter, etc.). An outer tube 16 may be disposed over inner tube 12, defining an inflation lumen 18 therebetween. A balloon 20 may be coupled to outer tube 16.

Support block 10 may have a number of beneficial uses, including maintenance of inflation lumen 18 during manufacturing and use of catheter 14. For example, inflation lumen 18 may be compressed or balloon 20 may become wrinkled (which may occlude inflation lumen 18 or decrease the fluid communication of inflation lumen 18 with balloon 20) when trying to pass catheter 14 through a tight stenosis or a total occlusion. Additionally, support block 10 may substantially prevent the displacement of balloon 20 relative to outer tube 16, prevent a marker band 22 from occluding inflation lumen 18, increase axial strength of catheter 14, enhance strain relief of catheter 14, etc. These and other uses may be found in the subsequent description.

Support block 10 may be comprised of polyether block amide (PEBA) which is commercially available from Atochem Polymers of Birdsboro, Pa., and sold under the trade name PEBAX; Grilamid® (ELY 2694), which is commercially available from EMS American Grilon; or nylon. Alternatively, support block 10 may be comprised of metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, perfluoro (propyl vinyl ether) (PFA), and combinations thereof. Alternative materials may be used for constructing support block 10 without departing from the spirit of the invention.

Support block 10 may further comprise a distal region 24 that may include a plurality of distal fins 26. Distal fins 26 may contact the interior surface of balloon 20 and may be collapsible. According to this embodiment, support block 10 may be able to assume a low profile appropriate for navigating catheter 14 through the vasculature of a patient. Collapsible distal fins 26 may also be useful for allowing fins 26 to be wrapped down onto inner tube 12 so that support block 10 may fit into inflation lumen 18 during the initial manufacturing of catheter 14. However, once support block 10 is positioned outside of inflation lumen 18 at a location within balloon 20, it would be preferred that support block 10 could not become repositioned within inflation lumen 18.

Support block 10 may be coupled to inner tube 12 at a location proximate to marker band 22. According to this embodiment, support block 10 may substantially minimize displacement of marker band 22 during a procedure that may distort balloon 20 or otherwise apply a force to marker band 22. This feature of support block 10 may be useful in preventing marker band 22 from moving proximally and occluding inflation lumen 18.

A number of manufacturing techniques may be used to couple support block 10 to inner tube 12. For example, support block 10 may be coupled to inner tube 12 by adhesive, direct molding of support block 10 onto inner tube 12, slidably disposing support block 10 onto inner tube 12, fusing support block 10 to inner tube 12, laser welding, heating shrinking, etc. A person of ordinary skill in the art may be familiar with a number of alternative methods for coupling support block 10 to inner tube 12 without departing from the scope of the invention.

Inner tube 12 may include a proximal end (not shown), a distal end (not shown), and a lumen 32 extending therethrough. Lumen 32 may comprise a guidewire lumen, wherein a guidewire 34 may be disposed. A number of materials may be used to manufacture inner tube 12, including stainless steel, nickel alloys, polymers, etc. Alternatively, materials including those listed above may be used.

Outer tube 16 may be disposed over inner tube 12, and may further comprise a proximal end (not shown), a distal end 38, and define inflation lumen 18 therebetween. Inflation lumen 18 may be in fluid communication with balloon 20. Outer tube 16 may be comprised of a metal, a metal alloy, a polymer, or other suitable materials including those listed above.

In addition to some of the utilities described above, support block 10 may also be useful for preventing deformation of sleeves used for delivering a stent. According to this embodiment, support block 10 (or a plurality of support blocks 10) may be disposed proximate the ends of the sleeve and may prevent the sleeves from folding back upon themselves when they are withdrawn from the stent or maintain lumen dimensionality during the process of coupling the sleeves to the stent. A description of the sleeves can be found in U.S. Pat. No. 4,950,227 to Savin et al., the entire disclosure of which is incorporated by reference.

FIG. 2 is a plan view of an alternative inner member support block according to a preferred embodiment of the invention. Support block 110 is similar to support block 10 and further comprises a proximal region 140 in addition to distal region 124 and distal fins 126. Preferably, at least a portion of proximal region 140 extends into inflation lumen 18.

Proximal region 140 may further comprise a plurality of proximal fins 142 (more clearly shown in FIG. 4) that may contact an interior surface of outer tube 16. According to this embodiment, contact between proximal region 140 and outer tube 16 may help maintain fluid communication between inflation lumen 18 and balloon 20. More particularly, support block 110 may help to maintain inflation lumen 18 during manufacturing of catheter 14 wherein balloon 20 may be coupled to outer tube 16 by heat bonding, laser welding, etc. The fins may also allow for the flow of inflation media (e.g., air, fluids, etc.) to freely pass from an inflation medium source disposed near proximal end 36 of outer tube 16 to balloon 20.

FIG. 3 is a perspective view of support block 10 according to a preferred embodiment of the invention. From this drawing, distal fins 26 may be seen as well as a plurality of distal valleys 44 located between fins 26. Distal valleys 44 may be useful for allowing fluid communication between inflation lumen 18 and balloon 20.

In a preferred embodiment, support block 10 may include six distal fins 26. However, it can be anticipated that any number of distal fins 26 may be used without departing from the spirit of the invention. For example, two, four, eight, etc. distal fins 26 may be used.

Support block 10 may further comprise a proximal end 46 and a distal end 48. Preferably, support block 10 may taper (i.e., decrease in outside diameter) from proximal end 46 to distal end 48. As support block 10 tapers, distal fins 26 may broaden such that the width of distal fins 26 near distal end 48 is greater than the width near proximal end 46. This taper may serve to increase perfusion from inflation lumen 18 into balloon 20 and may even permit perfusion when balloon 20 is collapsed onto support block 10.

FIG. 4 is a perspective view of support block 110 according to a preferred embodiment of the invention. From this drawing, not only can distal fins 126 and distal valleys 144 be seen, but also proximal fins 142, and a plurality of proximal valleys 150 may be seen between proximal fins 142. Proximal valleys 150 may be useful for maintaining fluid communication between inflation lumen 18 and balloon 20. Similar to what is described above, any number of proximal fins 142 (e.g., two, four, six, eight, etc.) may be used without departing from the spirit of the invention.

Support block 110 may further comprise an abutment surface 52. Abutment surface 52 may abut against distal end 38 of outer tube 16 and add further support during use of support block 110. For example, abutment surface 52 may minimize compression of balloon 18, compression of inner tube 12, and compression of outer tube 16. By minimizing compression, inflation lumen 18 may be maintained.

FIG. 5 is a cross-sectional view of inner member support block 10 taken proximate distal end 48. Because of the distal taper of support block 10, distal fins 42 may be seen in this drawing as distal-distal fins 54 (i.e., distal fins proximate distal end 48) and proximal-distal fins 56 (i.e., distal fins proximate proximal end 46). According to this embodiment, the broadening of distal fins 42 may be seen.

Reference numeral 58 refers to a phantom line representing the outside diameter of support block 10 near distal end 48 before distal valleys 44 are formed. From FIG. 5, it should be clear that the width of distal fins 26 broadens near distal end 48 and that, preferably, support block 10 tapers. Similar to what is described above, this taper may serve to increase perfusion from inflation lumen 18 into balloon 20 and may even permit perfusion when balloon 20 is collapsed onto support block 10.

FIG. 6 is a cross-sectional view of a second alternative inner member support block according to a preferred embodiment of the invention. Support block 210 may comprise four fins 260 separated by four valleys 262. According to a preferred embodiment, this cross section may represent a four-finned support block appropriate for multiple embodiments of the invention. For example, a four-finned support block may be used for distal region 24 of support block 10, proximal region 140 of support block 110, and combinations thereof.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An elongate medical device, comprising:
   an outer tubular member having a proximal end, a distal end and a lumen extending therethrough;
   an elongate shaft disposed within at least a portion of the lumen of the outer tubular member, the elongate shaft having a proximal end and a distal end;
   a balloon coupled to the distal end of the outer tubular member;
   an inflation lumen defined between the elongate shaft and the outer tubular member, the inflation lumen in fluid communication with the balloon; and
   a support block secured to the elongate shaft, the support block including a fluid passageway in fluid communication between the inflation lumen and the balloon, and an abutment surface abutting the distal end of the outer tubular member, wherein at least a portion of the support block extends distal of the distal end of the outer tubular member;
   wherein the support block further comprises a proximal region and a distal region, at least a portion of the proximal region having an outer diameter less than the lumen of the outer tubular member, and at least a portion of the distal region having an outer diameter greater than the lumen of the outer tubular member.

2. The elongate medical device of claim 1, wherein at least a portion of the proximal region is disposed within the inflation lumen.

3. The elongate medical device of claim 1, wherein the distal region is tapered.

4. The elongate medical device of claim 1, wherein the proximal region includes a plurality of proximal fins.

5. The elongate medical device of claim 1, wherein the distal region includes a plurality of distal fins.

6. The elongate medical device of claim 1, wherein the support block further comprises a plurality of valleys defining the fluid passageway.

7. The elongate medical device of claim 1, wherein the support block is movable relative to the outer tubular member.

8. The elongate medical device of claim 1, wherein at least a portion of the support block is disposed within the balloon.

9. The elongate medical device of claim 1, wherein the support block further comprises a proximal region having a plurality of proximal fins.

10. The elongate medical device of claim 9, wherein the plurality of proximal fins are collapsible.

11. The elongate medical device of claim 1, wherein the support block further comprises a distal region having a plurality of distal fins.

12. The elongate medical device of claim 11, wherein the plurality of distal fins are collapsible.

13. An elongate medical device, comprising:
    an outer tubular member having a proximal end, a distal end and a lumen extending therethrough;
    an elongate shaft disposed within at least a portion of the lumen of the outer tubular member, the elongate shaft having a proximal end and a distal end;
    a balloon coupled to the distal end of the outer tubular member;
    an inflation lumen defined between the elongate shaft and the outer tubular member, the inflation lumen in fluid communication with the balloon; and
    a support block secured to the elongate shaft proximate to the distal end of the outer tubular member and slidable relative to the outer tubular member, the support block including a fluid passageway providing fluid communication between the inflation lumen and the balloon:
    wherein the support block further comprises a proximal region and a distal region, at least a portion of the proximal region having an outer diameter less than the lumen of the outer tubular member, and at least a portion of the distal region having an outer diameter greater than the lumen of the outer tubular member.

14. The elongate medical device of claim 13, wherein the support block is capable of translatory motion relative to the outer tubular member.

15. The elongate medical device of claim 13, wherein the support block further comprises a plurality of valleys defining the fluid passageway.

16. The elongate medical device of claim 13, wherein the support block further comprises a plurality of fins.

17. The elongate medical device of claim 16, wherein the plurality of fins are longitudinal fins.

18. The elongate medical device of claim 16, wherein the plurality of fins are collapsible.

* * * * *

UNITED STATES PATENT AND TRADEMARK OFFICE
CERTIFICATE OF CORRECTION

PATENT NO. : 7,597,709 B2 Page 1 of 1
APPLICATION NO. : 11/093887
DATED : October 6, 2009
INVENTOR(S) : Richard L. Goodin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1225 days.

Signed and Sealed this

Twenty-eighth Day of September, 2010

David J. Kappos
*Director of the United States Patent and Trademark Office*